(12) United States Patent
Coufal

(10) Patent No.: US 6,586,629 B1
(45) Date of Patent: Jul. 1, 2003

(54) METHOD OF INTRODUCING MELAMINE OFF-GASES INTO A UREA PLANT

(75) Inventor: Gerhard Coufal, Leonding (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 09/856,193

(22) PCT Filed: Nov. 26, 1999

(86) PCT No.: PCT/EP99/09192

§ 371 (c)(1),
(2), (4) Date: May 18, 2001

(87) PCT Pub. No.: WO00/32566

PCT Pub. Date: Jun. 8, 2000

(30) Foreign Application Priority Data

Dec. 3, 1998 (AT) ................................................ 2039/98

(51) Int. Cl.⁷ .................... C07C 273/04; C07C 273/12; C07D 251/60
(52) U.S. Cl. .......................... 564/67; 544/201; 544/203
(58) Field of Search ................................. 544/201, 203; 564/67

(56) References Cited

U.S. PATENT DOCUMENTS 3,700,672 A * 10/1972 Kokubo et al. ............. 544/201
4,013,431 A * 3/1977 Berkel et al. .................. 55/70

FOREIGN PATENT DOCUMENTS

| EP | 0 727 414 | 8/1996 |
| WO | 98/08808 | 3/1998 |
| WO | 98/32731 | 7/1998 |

* cited by examiner

*Primary Examiner*—John M. Ford
*Assistant Examiner*—Venkataraman Balasubramanian
(74) *Attorney, Agent, or Firm*—Wenderoth, Lind & Ponack, L.L.P.

(57) ABSTRACT

The invention relates to a method for producing urea. According to said method, the off-gases which originate from a melamine plant and essentially consist of $NH_3$ and $CO_2$ are introduced into the high-pressure zone of the urea plant by means of ejectors.

9 Claims, 4 Drawing Sheets

METHOD OF INTRODUCING MELAMINE OFF-GASES INTO A UREA PLANT

Figure 1:
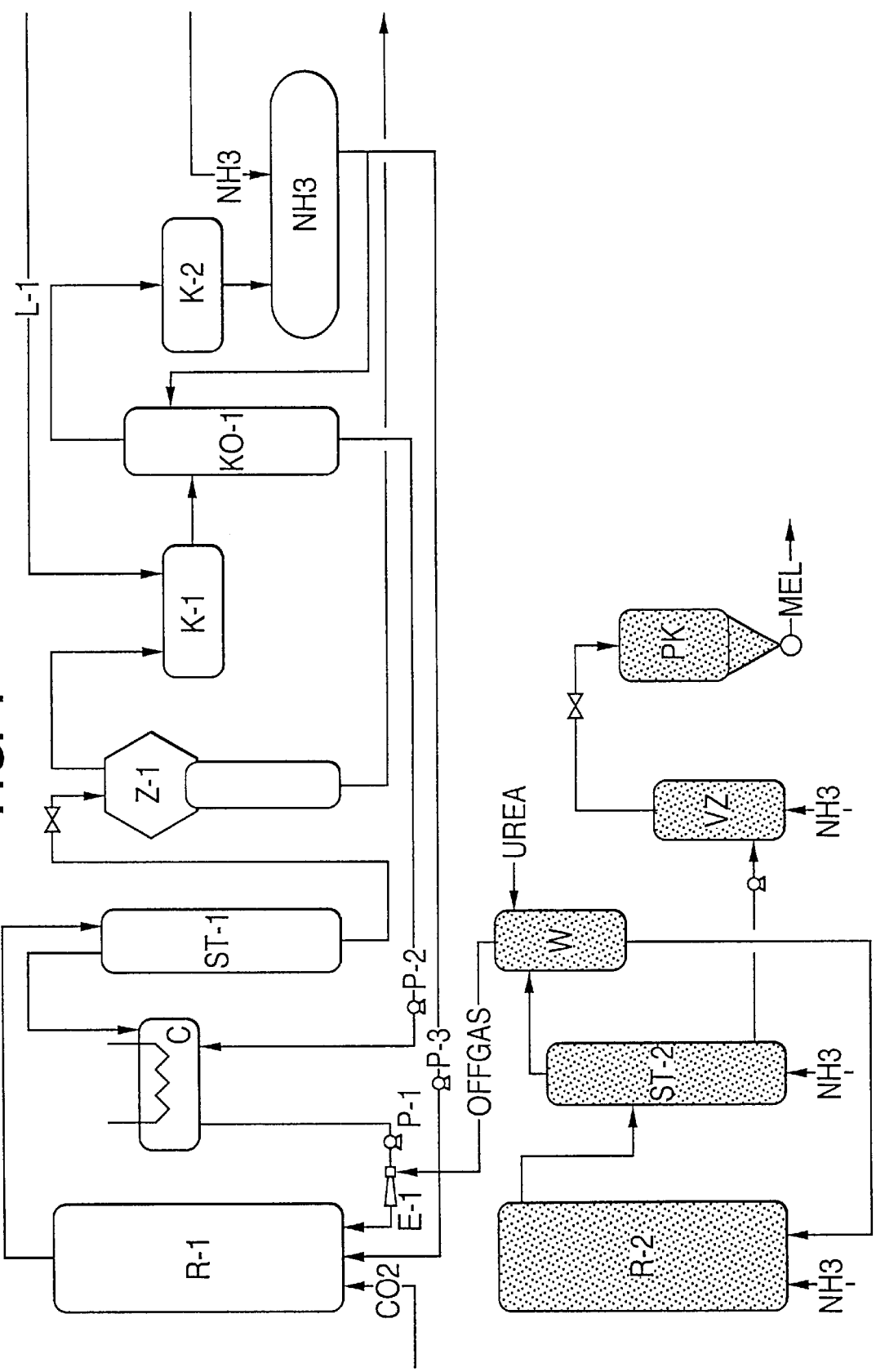

The invention relates to the introduction of melamine off-gases into a urea plant by means of ejectors.

The off-gases obtained in the melamine synthesis and comprising in particular $NH_3$ and $CO_2$ are usually used for the preparation of urea. Advantageously, the off-gases from the melamine plant are transferred directly into the urea plant, where, for example, they are absorbed in a carbamate stream and transported further into the reactor. An improved, more efficient and more economical method of off-gas introduction is described in K. Abe et al., Kagaku Kogaku 40, 298–302 (1976), in which the off-gases, optionally after removal of residual melamine in a urea scrubber, are introduced directly and unchanged, in the dry state, into the high-pressure zone of the urea plant. This process variant is also described in SU 899538 or WO 98/08808. According to WO 98/32731, the melamine off-gases are first condensed at the pressure of the melamine reactor, the ammonium carbamate formed then being transported into the high-pressure zone of the urea plant.

The disadvantage of the known methods is in particular that in some cases energy losses occur through pressure relief or cooling of the off-gases, with the resulting additional process steps and apparatus components, or that, in the case of direct transfer of the off-gases into the urea plant, the pressure of the off-gases or the pressure in the melamine reactor has to be greater than the pressure in the urea reactor. This necessitates an inflexible and rigidly specified procedure in the two reactors, with the result that the reactors often cannot be operated under the conditions optimal for the respective process.

It has now been found, unexpectedly, that these disadvantages can be eliminated when the melamine off-gases are introduced directly into the high-pressure zone of the urea plant by means of ejectors.

The invention accordingly relates to a method for producing urea, in which the gases (melamine off-gases) which originate from a melamine plant and substantially comprise $NH_3$ and $CO_2$ are introduced directly into the high-pressure zone of a urea plant by means of one or more ejectors. The high-pressure zone of the urea plant includes in particular the reactor, the stripper and the carbamate condenser, as well as lines and apparatus parts present in this region of the plant.

The present method is suitable for any desired melamine plants and urea plants. Such plants are known, for example, from "Ullmann's Encyclopedia of Industrial Chemistry, 5th ed., vol. A16 (1990), pages 171–185 (Melamine) and vol. A27 (1996), pages 333–365 (Urea), and from K. Abe et al., Kagaku Kogaku 40 (1976), pages 298–302, and from EP-727,414 A, WO 98/08808 and WO 98/32731.

The melamine off-gases used in the present method preferably originate from a melamine high-pressure plant in which melamine is obtained at temperatures of about 300–500° C. and pressures of about 80–800 bar from urea with elimination of $NH_3$ and $CO_2$. The off-gases eliminated and substantially comprising $NH_3$ and $CO_2$ are passed, according to the invention, directly into a urea plant, preferably after being passed through molten urea (urea scrubber) for removing residual melamine, as described, for example, in Ullmann. Particularly suitable urea plants are those which are based on the "urea-stripping process", the gases being converted into urea at about 150 to 350° C., preferably at about 170 to 200° C., and about 125 to 350 bar, preferably at about 140 to 200 bar. $NH_3$ and $CO_2$ not converted into urea is expelled in a downstream stripper and then condensed in a condenser, $NH_3$- and $CO_2$-containing ammonium carbamate being formed, which is recycled into the urea reactor. The urea solution emerging from the stripper is concentrated in further downstream decomposers at decreasing pressures, for example in a medium-pressure decomposer, then in a low-pressure decomposer and in a vacuum evaporator, by further decomposition of the carbamates and carbonates present and expulsion of $NH_3$ and $CO_2$. The gases obtained during the concentration are condensed and then recycled into the urea process.

In a preferred method according to the present invention, the ejectors for transporting the melamine off-gases into the high-pressure zone of the urea plant are operated with one or more of the following streams as driving media:
a) liquid $NH_3$,
b) gaseous $NH_3$ or $CO_2$,
c) aqueous solutions containing substantially $NH_3$ and $CO_2$.

The aqueous solutions containing substantially $NH_3$ and $CO_2$ are preferably obtained in a urea plant but they may also originate from other processes in which $NH_3$ and $CO_2$ are obtained, for example from a melamine plant. Aqueous solutions which originate in the preparation of urea, in particular from the working-up, contain substantially $NH_3$ and $CO_2$ and originate, for example, from the carbamate condenser or from the low-pressure zone of the urea plant, for example from the medium-pressure absorber, can be used according to the invention, as a driving medium for the ejectors for introducing the melamine off-gases into the high-pressure zone of the urea plant.

A particular advantage of using the solutions originating from the bottom of the medium-pressure absorber and also containing carbonates in addition to $NH_3$, $CO_2$, $H_2O$ and carbamates is that they have a low expulsion pressure of the dissolved gases. In fact, it proves advantageous if the gas expulsion pressure of the propellants, optionally also the temperature, are lower than the pressure and optionally the temperature of the melamine off-gases to be introduced. This prevents expulsion of dissolved gases in the ejector.

Depending on the type and amount of the driving medium, the pressure of the driving media used is such that as far as possible the total amount of off-gases obtained can be transported, depending on the suction conditions and the amount of the off-gases to be conveyed and on the respective counter-pressure in the high-pressure zone of the urea plant. The pressure and the amount of the driving media must accordingly be correspondingly high in order to ensure that the off-gases to be transported can be introduced in the respective amount at the respective pressure in the high-pressure zone of the urea plant. The pressure of the driving media is higher than the pressure in the high-pressure zone of the urea plant and is preferably from 1.1 to 3 times as high, particularly preferably from 1.3 to 2.5 times as high, as the pressure in the high-pressure zone of the urea plant. The temperature of the driving medium is in particular dependent on the respective procedure and is preferably in a range from about 10° C. to 200° C. In the case of the use of $NH_3$, for example of the synthesis $NH_3$ for the urea preparation, a temperature of from about 10° C. to 80° C., particularly preferably from about 20° C. to 65° C., proves advantageous. In the case of the use of synthesis $CO_2$, the temperature is preferably slightly higher, from about 115° C. to 140° C. $NH_3$- and $CO_2$-containing aqueous solutions as driving media which originate, for example, from the carbamate condenser of the urea plant, for example from 3 to 4 bar steam simultaneously being generated, preferably have temperatures of from about 150° C. to 160° C. Recycled carbonate solutions, for example from the medium-pressure absorber of the urea plant, can have temperatures of from about 65° C. to 100° C., preferably from about 65° C. to 70° C.

The molar ratio of $NH_3$ to $CO_2$ in the melamine off-gases to be introduced and originating from the melamine plant depends on the type of melamine process used and is preferably from about 2.5 to 5. The pressure of the melamine off-gases originating from the melamine plant corresponds substantially to the pressure in the melamine reactor and is preferably from about 50 to 250 bar, particularly preferably from about 70 to 200 bar. The temperature of the melamine off-gases is preferably from about 175 to 250° C., particularly preferably from about 180 to 210° C.

Accordingly, the particular advantage of the process according to the invention is in particular the use of the product streams to be recycled as ejector driving media and also the use of the $NH_3$ and $CO_2$, used as starting materials, as ejector driving media. Consequently, on the one hand, an economical procedure is achieved and, on the other hand, it is also possible to operate the urea and melamine production in a flexible manner and under optimum conditions in each case, melamine reactor pressures lower than urea reactor pressures also being possible.

FIG. 1 to FIG. 4 show, by way of example, 4 possible variants according to the invention for introducing the melamine off-gases into the urea reactor with the aid of ejectors. FIG. 1 to FIG. 4 show the following substantial parts of the urea plant and of the melamine plant:

Urea plant

R-1 Urea reactor
C Carbamate condenser
ST-1 Urea stripper
Z-1 Decomposer/separator
K-1 Condenser 1
K-2 Condenser 2
K O-1 Medium-pressure absorber
E-1 Ejector 1
E-2 Ejector 2
E-3 Ejector 3
P-1 Carbamate pump
P-2 Carbonate pump
P-3 $NH_3$ pump Melamine plant R-2 Melamine reactor
ST-2 Melamine stripper
W Urea scrubber
VZ Dwell tank
PK Product cooler

EXAMPLE 1

In a plant as shown schematically in FIG. 1, the reaction products are fed from the top of the urea reactor R-1 to a steam-heated falling-film stripper ST-1, where the $CO_2$ content of the solution entering is stripped from the solution by boiling $NH_3$. The stripped gases with the solution recycled from the absorption column KO-1 (medium-pressure absorber) are fed to the carbamate condenser C and condensed there. The pressure of the condensate is increased by means of the pump P-1, and the condensate is then used as a driving medium for the ejector E1 in order to be able to transport the off-gases originating from the melamine plant into the urea reactor R-1. A solution having a lower $CO_2$ content then leaves the stripper ST-1 at the bottom and is let down from there into the separator. Most of the remaining carbamate is then decomposed in the steam-heated lower part of the separator, the falling-film decomposer Z-1, and the $NH_3$- and $CO_2$-rich gases are partially absorbed, in the medium-pressure condenser K-1, in an aqueous carbonate solution which originates, via L-1, from the low-pressure zone of the urea plant. The gas/liquid mixture from the condenser K-1 is fed into the medium-pressure absorber KO-1 and remaining $CO_2$ and $H_2O$ are washed out with liquid $NH_3$. At the bottom of KO-1, a solution is taken off and is recycled via the pump P-2 into the carbamate condenser C. The top product of KO-1, pure $NH_3$ gas, is condensed in the condenser K-2 and is fed into the temporary $NH_3$ storage tank.

EXAMPLE 2

Figure 2:
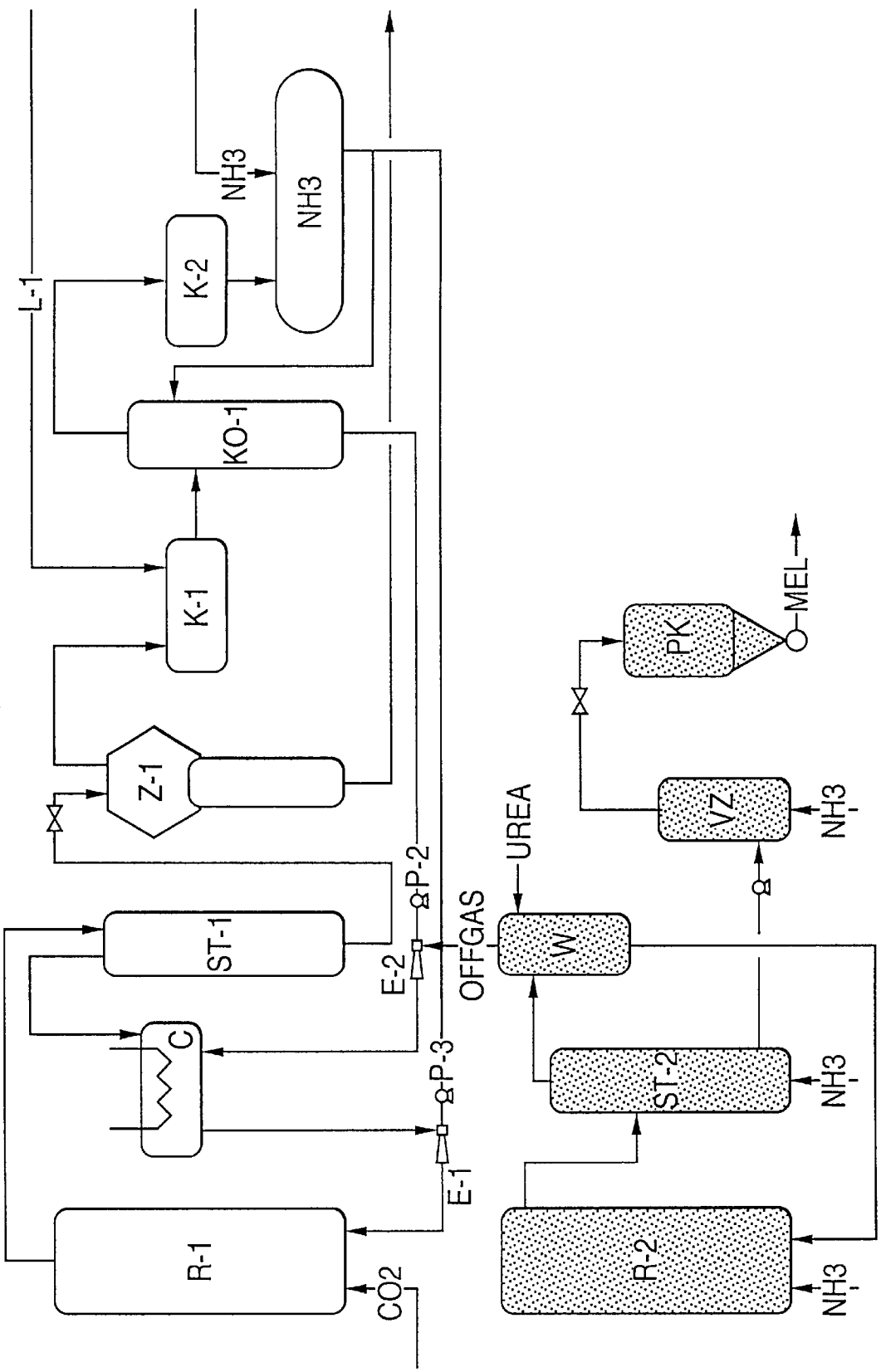

In a plant as shown schematically in FIG. 2, the reaction products are fed from the top of the urea reactor R-1 to a steam-heated falling-film stripper ST-1, where the $CO_2$ content of the solution entering is stripped from the solution by boiling $NH_3$. The stripped gases are fed into the carbamate condenser C. The pressure of the solution to be recycled and originating from the absorption column KO-1 is increased by means of the pump P-2 and then used as a driving medium for the ejector E-2, in order to be able to transport the off-gases originating from the melamine plant into the carbamate condenser C. In the carbamate condenser, the off-gases are condensed together with the gases arriving from the stripper ST-1. A solution having a lower $CO_2$ content then leaves the stripper ST-1 at the bottom and is let down from there into the separator. In the steam-heated lower part of the falling-film decomposer Z-1, most of the remaining carbamate is then decomposed and the $NH_3$- and $CO_2$-rich gases are partially absorbed, in the medium-pressure condenser K-1, in an aqueous carbonate solution which originates via L-1 from the low-pressure zone of the urea plant. The gas-liquid mixture from K-1 is fed into the medium-pressure absorber KO-1 and remaining $CO_2$ and $H_2O$ are washed out with liquid $NH_3$. At the bottom of KO-1, a solution is taken off and is recycled via the pump P-2 and ejector E-2 into the carbamate condenser C. The top product of KO-1, pure $NH_3$ gas, is condensed in the condenser K-2 and fed into the temporary $NH_3$ storage tank. Liquid $NH_3$ is withdrawn from the temporary storage tank, its pressure is increased by means of the pump P-3 and it is then used as the driving medium for ejector E-1 in order thus to be able to transport the condensate arriving from the carbamate condenser C into the urea reactor.

EXAMPLE 3

Figure 3:
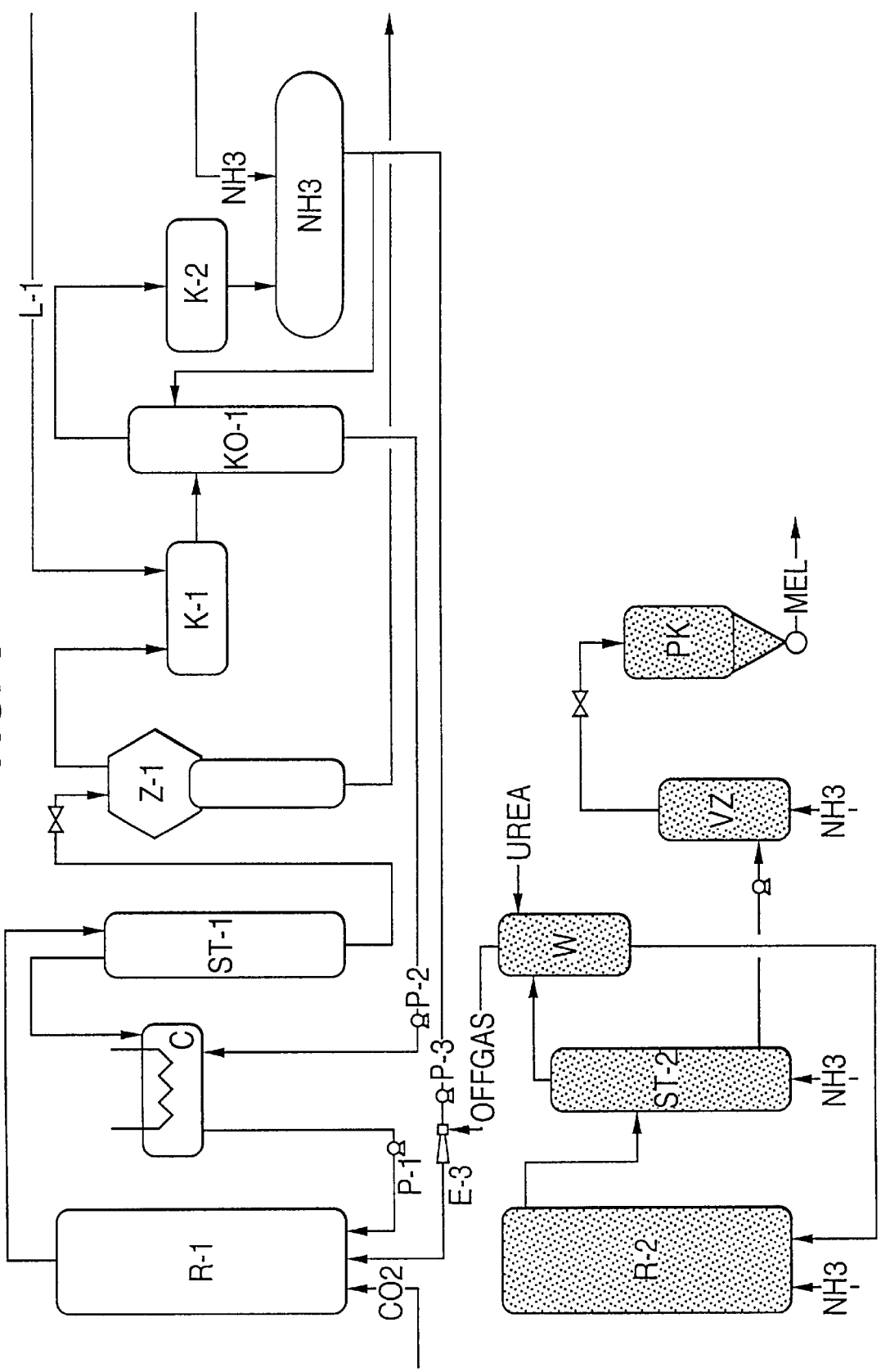

In a plant as shown schematically in FIG. 3, the reaction products from the top of the urea reactor R-1 are fed to a steam-heated falling-film stripper ST-1, where the $CO_2$ content of the solution entering is stripped from the solution by boiling $NH_3$. The stripped gases with the solution recycled from the absorption column KO-1 by means of P-2 are fed into the carbamate condenser C and condensed there. The pressure of the condensate is increased after the condenser by means of the pump P-1 and the condensate is then transported into the urea reactor R-1. A solution having a lower $CO_2$ content then leaves the stripper ST-1 at the bottom and is let down from there into the separator. In the steam-heated lower part of the separator, the falling-film decomposer Z-1, most of the remaining carbamate is then decomposed, and the $NH_3$- and $CO_2$-rich gases are partially absorbed, in the medium-pressure condenser K-1, in an aqueous carbonate solution which originates via L-1 from the low-pressure zone of the urea plant. The gas-liquid mixture from K-1 is fed into the medium-pressure absorber KO-1 and remaining $CO_2$ and $H_2O$ are washed out with liquid $NH_3$. A solution is withdrawn from the bottom of KO-1 and is recycled via the pump P-2 into the carbamate condenser C. The top product of KO-1, pure $NH_3$ gas, is condensed in the condenser K-2 and fed into the temporary $NH_3$ storage tank. The off-gases originating from the melamine plant are transported via the ejector E-3 into the urea reactor.

The driving medium for E-3 is liquid $NH_3$ from the $NH_3$ tank, the pressure of which is boosted by means of the pump P-3.

EXAMPLE 4

Figure 4:
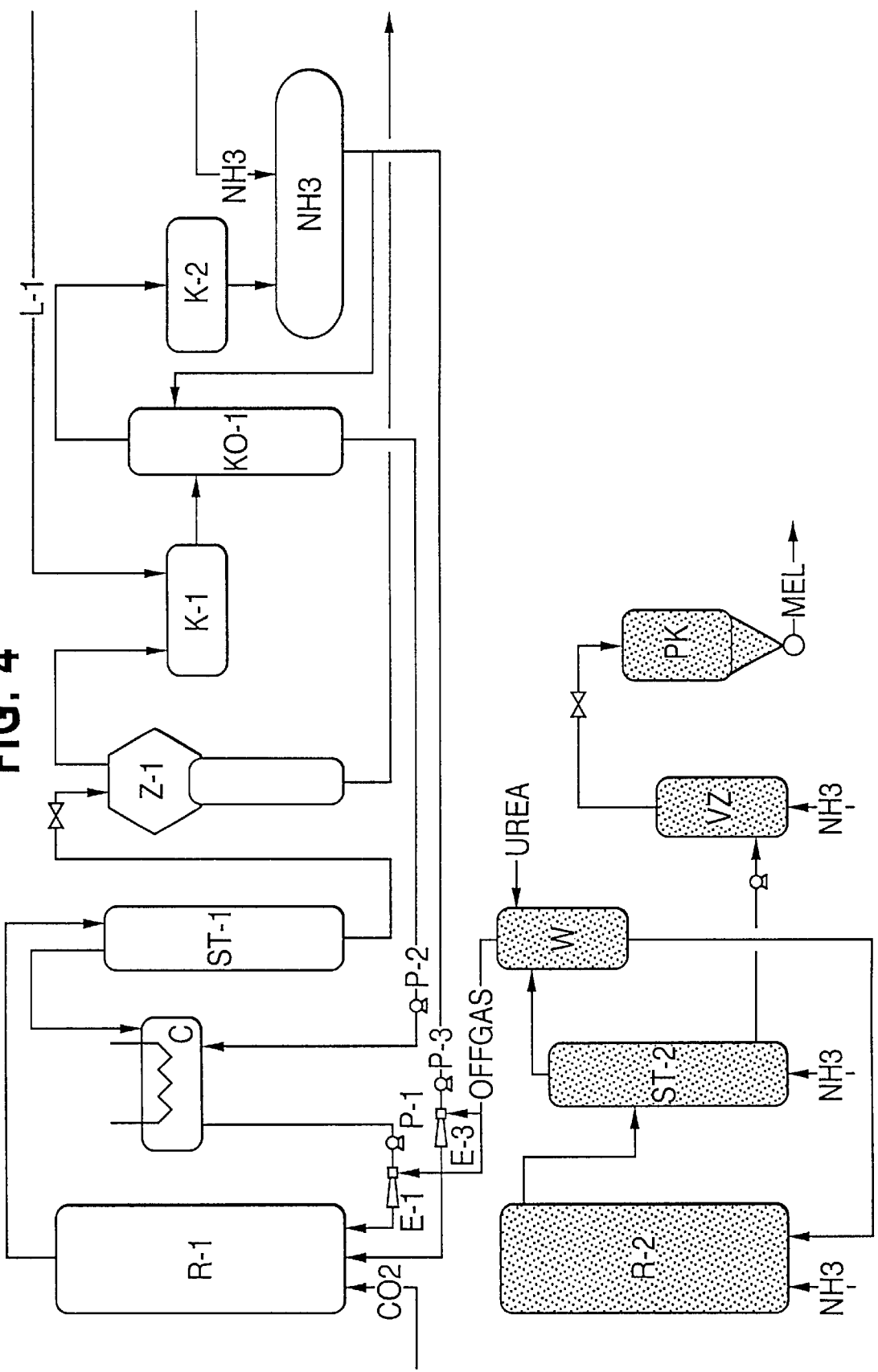

In a plant as shown schematically in FIG. 4, the off-gases are transported into the urea reactor by means of two ejectors (E-1 and E-3) in a combination of the procedures described in Examples 1 and 3. The driving medium for E-1 is the condensate from the carbamate condenser, analogously to Example 1, and the driving medium for E-2 is liquid $NH_3$ from the $NH_3$ tank, analogously to Example 3.

What is claimed is:

1. Method for producing urea, in which the gases originating from a melamine plant and substantially comprising $NH_3$ and $CO_2$ are introduced directly into a high-pressure zone of a urea plant by means of one ejector or more, the ejector(s) being driven by one or more of the following as driving media:

a) liquid $NH_3$,
   b) gaseous $NH_3$ or $CO_2$,
   c) substantially $NH_3$- and $CO_2$-containing aqueous solutions, whereby one or more of said driving media is a process stream of the urea or the melamine plant.

2. Method according to claim 1, in which the gases originating from the melamine plant have a pressure which substantially corresponds to the pressure in the melamine reactor.

3. Method according to claim 1, in which the gases originating from the melamine plant have a pressure of from about 50 to 250 bar and a temperature of from about 175 to 250° C.

4. Method according to claim 4, in which the gases originating from the melamine plant have a pressure of from about 70 to 200 bar and a temperature of from about 180 to 210° C.

5. Method according to claim 1, in which the pressure of the driving medium is higher than the pressure in the high-pressure zone of the urea plant.

6. Method according to claim 5, in which the pressure of the driving media is substantially from about 1.1 to 3 times as high as the pressure in the high-pressure zone of the urea plant.

7. Method according to claim 1, in which the pressure in the high-pressure zone of the urea plant is substantially from about 125 to 350 bar and the temperature from about 150 to 350° C.

8. Method according to claim 7, in which the pressure in the high-pressure zone of the urea plant is substantially from about 140 to 200 bar and the temperature from about 150 to 210° C.

9. Method according to claim 5, in which the pressure of the driving media is substantially from about 1.3 to 2.5 times as high as the pressure in the high-pressure zone of the urea plant.

* * * * *